US010687838B2

(12) United States Patent
Augustin et al.

(10) Patent No.: US 10,687,838 B2
(45) Date of Patent: Jun. 23, 2020

(54) INFLATABLE BALLOON FOR MEDICAL USE

(71) Applicants: DIANOSIC, Malakoff (FR); UNIVERSITE DE STRASBOURG, Strasbourg (FR); INSTITUT NATIONAL DE LA SANTE ET DE LA RECHERCHE MEDICALE, Paris (FR); HOPITAUX UNIVERSITAIRES DE STRASBOURG, Strasbourg (FR)

(72) Inventors: Marc Augustin, Paris (FR); Christian Debry, Paris (FR)

(73) Assignees: DIANOSIC, Malakoff (FR); UNIVERSITE DE STRASBOURG, Strasbourg (FR); INSTITUT NATIONAL DE LA SANTE ET DE LA RECHERCHE MEDICALE, Paris (FR); HOPITAUX UNIVERSITAIRES DE STRASBOURG, Strasbourg (FR)

(*) Notice: Subject to any disclaimer, the term of this patent is extended or adjusted under 35 U.S.C. 154(b) by 290 days.

(21) Appl. No.: 15/768,738

(22) PCT Filed: Oct. 14, 2016

(86) PCT No.: PCT/FR2016/052661
§ 371 (c)(1),
(2) Date: Apr. 16, 2018

(87) PCT Pub. No.: WO2017/064437
PCT Pub. Date: Apr. 20, 2017

(65) Prior Publication Data
US 2018/0310947 A1 Nov. 1, 2018

(30) Foreign Application Priority Data
Oct. 16, 2015 (FR) ...................... 15 59917

(51) Int. Cl.
A61B 17/24 (2006.01)
A61B 17/12 (2006.01)
(Continued)

(52) U.S. Cl.
CPC .......... *A61B 17/24* (2013.01); *A61B 1/00082* (2013.01); *A61B 17/12104* (2013.01);
(Continued)

(58) Field of Classification Search
CPC .............. A61B 17/12136; A61B 17/24; A61B 1/00082; A61B 2017/00296; A61B 17/12022
See application file for complete search history.

(56) References Cited

U.S. PATENT DOCUMENTS 2,265,387 A 12/1941 McMillin
3,516,407 A 6/1970 Ruggero
(Continued)

FOREIGN PATENT DOCUMENTS

DE 299 23 582 U1 12/2000
WO 96/39218 A1 12/1996
WO WO-9639218 A1 * 12/1996 ....... A61B 17/12136

OTHER PUBLICATIONS

International Search Report, dated Feb. 23, 2017, from corresponding PCT/FR2016/052661 application.

Primary Examiner — Shaun L David
Assistant Examiner — Christina C Lauer
(74) Attorney, Agent, or Firm — Young & Thompson

(57) ABSTRACT

Disclosed is an inflatable balloon for medical use, intended to be inserted deflated into a human or animal body cavity and then inflated once inside this cavity so as to apply pressure against the cavity. The inflatable balloon includes a balloon body, the wall of which is made from a flexible inflatable material, the balloon body having a generally
(Continued)

Figure 5:
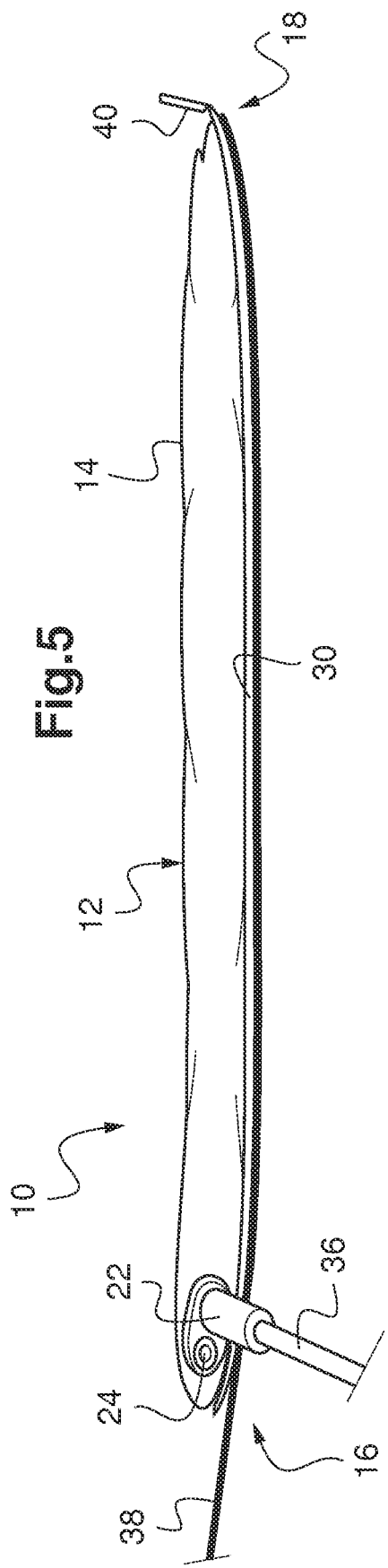

elongated shape with a proximal inflation end and a distal positioning end at the back of the cavity. It further includes an inflation opening formed in the proximal end through which a fluid is introduced into the balloon body so as to inflate it under pressure. The wall of the balloon body locally has an elongated portion called the sole that is stiffer than the rest of the wall, this sole extending from the proximal end to the distal end.

20 Claims, 2 Drawing Sheets

(51) Int. Cl.
*A61M 25/10* (2013.01)
*A61B 1/00* (2006.01)
*A61B 17/00* (2006.01)

(52) U.S. Cl.
CPC . *A61B 17/12136* (2013.01); *A61M 25/10185* (2013.11); *A61B 2017/00296* (2013.01); *A61M 2025/1084* (2013.01)

(56) References Cited

U.S. PATENT DOCUMENTS

| | | | |
|---|---|---|---|
| 3,570,494 A * | 3/1971 | Gottschalk | A61B 17/12022 606/196 |
| 5,139,510 A | 8/1992 | Goldsmith, III et al. | |
| 5,762,604 A * | 6/1998 | Kieturakis | A61B 17/00008 600/104 |
| 2004/0210278 A1* | 10/2004 | Boll | A61B 18/24 607/89 |
| 2015/0005805 A1 | 1/2015 | Kesten et al. | |

* cited by examiner

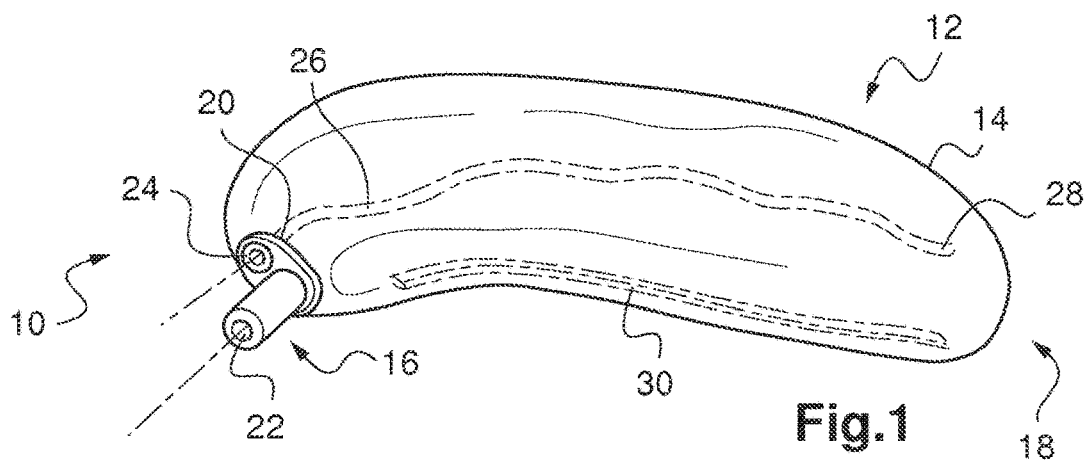
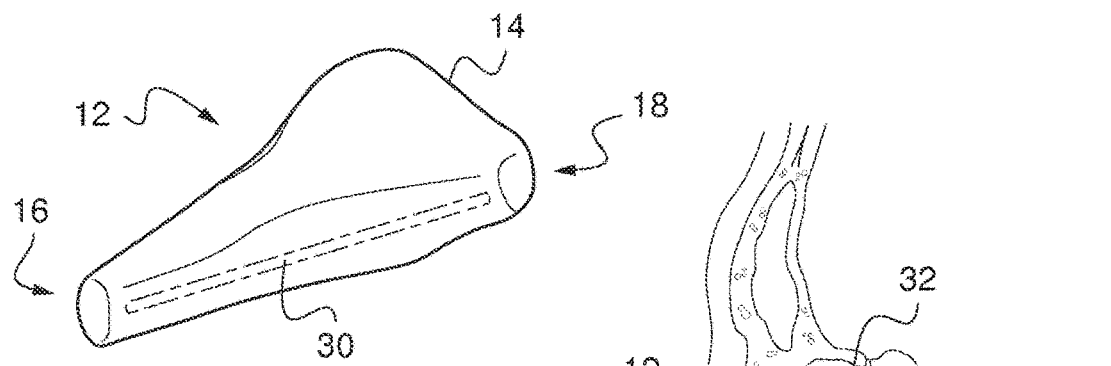
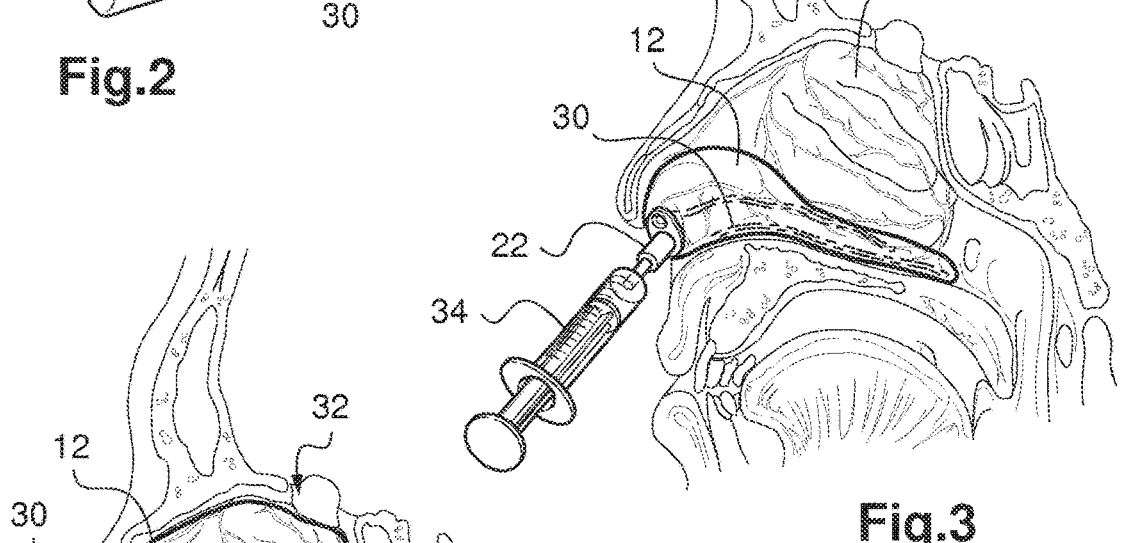
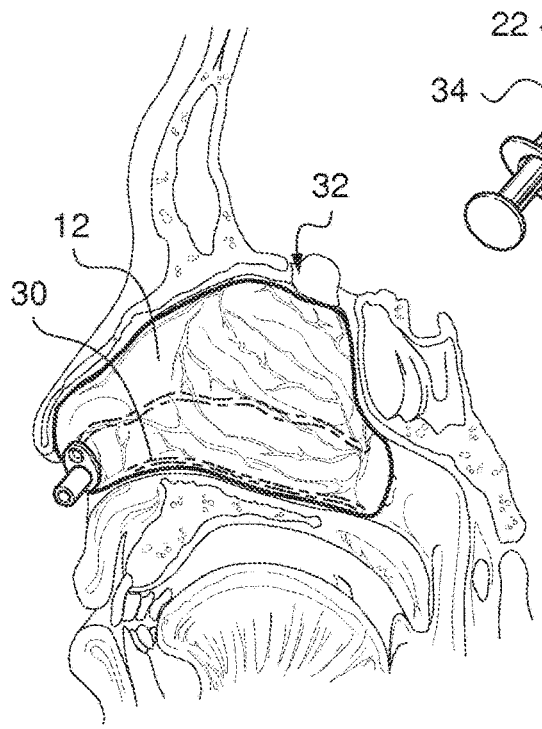

INFLATABLE BALLOON FOR MEDICAL USE

This invention relates to an inflatable balloon for medical use, intended to be inserted deflated into a human or animal body cavity and then inflated once inside this cavity so as to apply pressure against the walls of said cavity.

For example, in otorhinolaryngology, a balloon of this type is inserted into the nasal cavity of a patient and then once correctly positioned, it is inflated using a fluid such as air or gelled water. One frequent application of this type of balloon is the treatment of hemorrhages by pressure against the internal walls of the nasal cavity.

The invention relates more particularly to a balloon for medical use, comprising:
- a balloon body, the wall of which is made from a flexible inflatable material, with a generally elongated shape having a proximal inflation end and a distal positioning end at the back of the cavity, and
- an inflation opening formed in the proximal end through which a fluid is introduced into the balloon body so as to inflate it under pressure.

One difficulty with the use of this type of balloon is insertion and positioning of the balloon in the cavity, particularly in the case of insertion into a nasal cavity.

This difficulty is generally overcome by the use of rigid spacers to facilitate insertion of the balloon or even to replace the balloon, or the use of a movable rigid guide fixed to the balloon. Finally, the balloon is sometimes installed around a central tube, often a through tube through which the patient can breathe, this central tube then acting as a guide during insertion of the deflated balloon into the cavity. Such solutions are well known and for example are disclosed in patent documents such as U.S. Pat. Nos. 2,265,387, 3,516,407 and 5,139,510.

But either manipulation or the design, or both, of these different solutions is (are) complex.

It may thus be desirable to use an inflatable balloon for medical use that makes it possible to overcome at least some of the above-mentioned problems and constraints.

Therefore an inflatable balloon for medical use is disclosed comprising:
- a balloon body, the wall of which is made from a flexible inflatable material, with a generally elongated shape having a proximal inflation end and a distal positioning end at the back of the cavity, and
- an inflation opening formed in the proximal end through which a fluid is introduced into the balloon body so as to inflate it under pressure, wherein the wall of the balloon body locally has an elongated portion called the sole that is stiffer than the rest of the wall, this sole extending from the proximal end to the distal end.

Thus, the design of the proposed device is simple because the sole forms a portion of the wall of the balloon body. It is also easy to use because this stiffer sole facilitates insertion and correct positioning of the balloon over its entire length in the cavity.

Optionally, the sole is an add-on part in contact with the wall of the balloon body.

Also optionally, the sole is made of the same material as the rest of the wall of the balloon body, but it is significantly thicker than the rest of this wall.

Also optionally, an inflatable balloon for medical use according to the invention may further comprise a stiffener at the distal end prolonging the sole, this distal stiffener also being stiffer that the rest of the wall of the balloon body and being shaped so as to prevent any elongation of the balloon during its inflation, in cooperation with the sole.

Also optionally, an endoscope opening is further formed in the proximal end, this endoscope opening being designed for the introduction of an endoscope into the balloon body.

Also optionally, the endoscope opening comprises a valve for the insertion of an endoscope while preventing any outlet of fluid.

Also optionally, the endoscope opening leads into the inside of the balloon body at the inside of an elongated sock.

Also optionally, the elongated sock extending into the inside of the balloon body has a closed distal end not fixed to the wall of the balloon body.

Also optionally, an inflatable balloon for medical use according to the invention can be used in otorhinolaryngology. In this case, the balloon body can be preformed to match the internal shapes of a nasal cavity of a human or animal body when it is inflated.

Also optionally, an inflatable balloon for medical use according to the invention can further comprise a removable rigid insertion rod extending outwards along the prolongation of an end piece of the inflation opening and a removal rigid placement wire extending along the sole or inside the sole.

Figure 6:
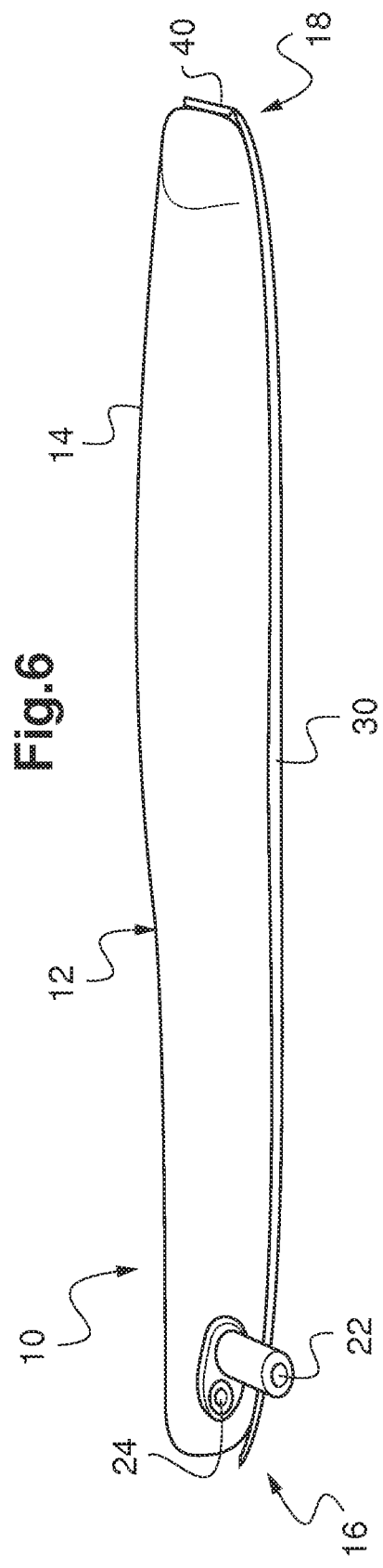

The invention will be better understood with reference to the following description, given purely as an example, with reference to the appended drawings in which:

FIG. 1 diagrammatically represents the general structure of an inflatable balloon for medical use, according to one embodiment of the invention, FIG. 2 illustrates an example shape for the balloon in FIG. 1, FIGS. 3 and 4 illustrate arrangements of the balloon in FIG. 1 in a nasal cavity, before and after inflation, and FIGS. 5 and 6 diagrammatically represent the general structure of an inflatable balloon for medical use according to another embodiment of the invention, before and after inflation.

The inflatable balloon 10 for medical use diagrammatically shown on FIG. 1 comprises a balloon body 12, the wall 14 of which is made of a flexible inflatable material, for example made of silicone or any equivalent material with these properties. It is intended to be inserted deflated into a human or animal body cavity and then inflated once inside this cavity so as to apply pressure against it. It has a generally elongated shape having a proximal inflation end 16 and a distal positioning end 18 at the back of the cavity. The outside of the wall 14 is advantageously coated with a sliding product that is not aggressive towards the biological tissues of the cavity.

The proximal end 16 comprises a rigid support 20 that has a first opening and an inflation end piece 22 leading to this first opening. This end piece 22 facilitates the introduction of a syringe to inflate the balloon body 12 under pressure using a fluid such as air, gelled water or any other appropriate fluid. It may be fitted with a valve or any appropriate system for inflation, so as to enable injection or suction of fluid without any leaks when the syringe or inflation device is removed.

The rigid support 20 is also optionally provided with a second opening 24 that will be used for the insertion of an endoscope into the balloon body 12. This second opening 24 may for example be in the form of a valve or any system for the insertion of an endoscope while preventing any fluid introduced into the balloon body 12 from escaping from it.

In this case, it is advantageous or even necessary for the fluid to be as transparent or translucent as possible to enable better observation of the environment by the endoscope inside the balloon 10.

In this case also, the balloon 10 may also comprise an elongated sock 26 extending into the inside of the balloon body 12 and having a closed distal end 28 not fixed to the wall 14 of the balloon body 12. An elongated sock must be understood to mean an elongated hood, with a shape complementary to the shape of the endoscope, into which the second opening 24 leads. It enables insertion of the endoscope without the endoscope coming into contact with the fluid present in the balloon body 12. It is advantageously formed from a possibly elastic flexible material, for example made of silicon or any other material with a similar nature.

According to the invention, the wall 14 of the balloon body 12 has a locally elongated portion 30 called the sole that is stiffer than the rest of the wall 14, this sole 30 extending from the proximal end 16 to the distal end 18. It forms the bottom of the balloon body 12, facilitating the insertion of the balloon 10 into the required cavity and its support even when the balloon is deflated. It also performs a guide function during inflation of the balloon 10, giving it a prestressed direction.

In practice, the sole 30 may be an add-on part in contact with the wall 14 of the balloon body 12, composed of any material providing the required stiffening function. This material can be chosen non-limitatively from among polymers such as polyvinyl chloride, polysiloxane, polyurethane, polyethylene polycarbonate, methyl polymethacrylate, ethylene polyterephthalate, or from among fluoropolymers such as polytetrafluoroethylene or polychlorotrifluoroethylene. Alternatively, it can be made from the same material as the rest of the wall 14 of the balloon body 12, but it is then significantly thicker than the rest of this wall 14 to make it stiffer.

As illustrated on FIG. 2, the balloon 10 may be designed for use in otorhinolaryngology. In this case, the wall 14 of the balloon body 12 can be preformed to match the internal shapes of a nasal cavity of a human or animal body in its inflated shape.

FIG. 3 illustrates the position of the balloon 10 in FIGS. 1 and 2 in a nasal cavity 32, in its deflated shape. Since the sole 30 is stiffer than the rest of the wall 14 of the balloon body 12, the balloon 10 is easily inserted into the nasal cavity 32. Once in position, a fluid is inserted through the end piece 22 into the balloon body 12 using a syringe 34. In this way, it is easy to control the pressure inside the balloon body.

This enables inflation of the balloon 10 until the result illustrated on FIG. 4 is obtained according to which the balloon body 12 occupies the entire internal space in the nasal cavity 32, matching the shape of its walls.

According to another embodiment illustrated in FIG. 5, and using the same references as mentioned above for unchanged elements, the balloon 10 also comprises a removal rigid insertion rod 36 extending outwards along the prolongation of the end piece 22. This rigid rod 36 facilitates installation of the balloon 10 in the cavity and can be broken or withdrawn once this installation has been made correctly. The balloon 10 can be inflated by means of the syringe 34 before or after this maneuver.

The balloon 10 in this other embodiment also comprises a removable rigid placement wire 38, extending as reinforcement to the sole 30 along or inside this sole. For example, it may be designed from a nickel-titanium alloy, this material having interesting shape memory and elasticity properties.

Finally, the balloon 10 in this other embodiment comprises a stiffener 40 at the distal end 18 along the prolongation of the sole 30. Like the sole 30, the stiffness of this distal stiffener 40 is higher than the stiffness of the rest of the wall 14 of the balloon body 12 and, for example, is positioned at an angle from the sole 30 equal to about 90°, so as to work in cooperation with the sole to prevent any elongation of the balloon 10 during inflation. Specifically, it may be composed of a piece added onto the distal end of the sole 30, composed of any material forming the required stiffness function. This material can be chosen non-limitatively from among polymers such as polyvinyl chloride, polysiloxane, polyurethane, polyethylene polycarbonate, methyl polymethacrylate, ethylene polyterephthalate, or from among fluoropolymers such as polytetrafluoroethylene or polychlorotrifluoroethylene.

The balloon 10 of this other embodiment is shown in its deflated shape in FIG. 5 and in its inflated shape with the rigid rod 36 and the removable rigid wire 38 withdrawn in FIG. 6.

It can clearly be seen that it is easy to insert the inflatable balloon for medical use as described above into a required cavity of a human being or an animal and to put it into position.

Considering its simple structure, its design and fabrication are easy so that it can be used once and then discarded.

It is particularly suitable for medical otorhinolaryngological, cervico-facial or neurological surgical operations. It can also be used in other surgical operations, particularly in orthopedics or digestive surgery. Without even considering surgery, it can also be used as a simple compression device to treat all sorts of epistaxies or bleeding of nasal cavities, such bleeding often occurring for example during consultations.

It will also be noted that the invention is not restricted to the embodiments described above.

In particular, the shapes of the sole 30 and the distal stiffener 40 may be adapted to any required application. Therefore applications are potentially very varied.

It will more generally be clear to an expert in the field that various modifications can be made to the embodiments described above, making use of the information disclosed above. The terms used in the following claims must not be interpreted as limiting the claims for the embodiments presented in this description, but must be interpreted to include all equivalents that the claims are intended to cover as a result of their formulation and that can be designed by an expert in the subject applying his own general knowledge to implementation of the information disclosed above.

The invention claimed is:

1. An inflatable balloon (10) for medical use, intended to be inserted deflated into a human or animal body cavity and then inflated once inside the cavity so as to apply pressure against it, comprising
    a balloon body (12), the wall (14) of which is made from a flexible inflatable material, with a generally elongated shape having a proximal inflation end (16) and a distal positioning end (18) at the back of the cavity, wherein the wall (14) further locally has an elongated portion (30) called the sole that is stiffer than the rest of the wall (14), this sole extending from the proximal end (16) to the distal end (18), an inflation opening (22) formed in the proximal end (16) through which a fluid is introduced into the balloon body (12) so as to inflate it under pressure, and an endoscope opening (24) further formed in the proximal end (16), this endoscope opening (24) being designed for the introduction of an endoscope into the balloon body (12), wherein the endoscope opening (24) leads into the inside of the balloon body (12) at the inside of an elongated sock (26) that has a closed distal end (28) not fixed to the wall (14) of the balloon body (12).

2. The inflatable balloon (10) for medical use according to claim 1, wherein the sole (30) is an add-on part in contact with the wall (14) of the balloon body (12).

3. The inflatable balloon (10) for medical use according to claim 2, further comprising a stiffener (40) at the distal end prolonging the sole (30), this distal stiffener (40) also being stiffer that the rest of the wall (14) of the balloon body (12) and being shaped so as to prevent any elongation of the balloon (10) during its inflation, in cooperation with the sole (30).

4. The inflatable balloon (10) for medical use according to claim 2, wherein the endoscope opening (24) comprises a valve for the insertion of an endoscope while preventing any outlet of fluid.

5. The inflatable balloon (10) for medical use according to claim 2, for use in otorhinolaryngology, wherein the balloon body (12) is preformed to match the internal shapes of a nasal cavity (32) of a human or animal body when it is inflated.

6. The inflatable balloon (10) for medical use according to claim 2, further comprising a removable insertion rod (36) extending outwards along the prolongation of an end piece of the inflation opening (22) and a removal placement wire (38) extending along the sole (30) or inside the sole.

7. The inflatable balloon (10) for medical use according to claim 1, wherein the sole (30) is made of the same material as the rest of the wall (14) of the balloon body (12), but it is significantly thicker than the rest of this wall (14).

8. The inflatable balloon (10) for medical use according to claim 7, further comprising a stiffener (40) at the distal end prolonging the sole (30), this distal stiffener (40) also being stiffer that the rest of the wall (14) of the balloon body (12) and being shaped so as to prevent any elongation of the balloon (10) during its inflation, in cooperation with the sole (30).

9. The inflatable balloon (10) for medical use according to claim 7, wherein the endoscope opening (24) comprises a valve for the insertion of an endoscope while preventing any outlet of fluid.

10. The inflatable balloon (10) for medical use according to claim 7, for use in otorhinolaryngology, wherein the balloon body (12) is preformed to match the internal shapes of a nasal cavity (32) of a human or animal body when it is inflated.

11. The inflatable balloon (10) for medical use according to claim 7, further comprising a removable insertion rod (36) extending outwards along the prolongation of an end piece of the inflation opening (22) and a removal placement wire (38) extending along the sole (30) or inside the sole.

12. The inflatable balloon (10) for medical use according to claim 1, further comprising a stiffener (40) at the distal end prolonging the sole (30), this distal stiffener (40) also being stiffer that the rest of the wall (14) of the balloon body (12) and being shaped so as to prevent any elongation of the balloon (10) during its inflation, in cooperation with the sole (30).

13. The inflatable balloon (10) for medical use according to claim 12, wherein the endoscope opening (24) comprises a valve for the insertion of an endoscope while preventing any outlet of fluid.

14. The inflatable balloon (10) for medical use according to claim 12, for use in otorhinolaryngology, wherein the balloon body (12) is preformed to match the internal shapes of a nasal cavity (32) of a human or animal body when it is inflated.

15. The inflatable balloon (10) for medical use according to claim 12, further comprising a removable insertion rod (36) extending outwards along the prolongation of an end piece of the inflation opening (22) and a removal placement wire (38) extending along the sole (30) or inside the sole.

16. The inflatable balloon (10) for medical use according to claim 1, wherein the endoscope opening (24) comprises a valve for the insertion of an endoscope while preventing any outlet of fluid.

17. The inflatable balloon (10) for medical use according to claim 16, for use in otorhinolaryngology, wherein the balloon body (12) is preformed to match the internal shapes of a nasal cavity (32) of a human or animal body when it is inflated.

18. The inflatable balloon (10) for medical use according to claim 16, further comprising a removable insertion rod (36) extending outwards along the prolongation of an end piece of the inflation opening (22) and a removal placement wire (38) extending along the sole (30) or inside the sole.

19. The inflatable balloon (10) for medical use according to claim 1, for use in otorhinolaryngology, wherein the balloon body (12) is preformed to match the internal shapes of a nasal cavity (32) of a human or animal body when it is inflated.

20. The inflatable balloon (10) for medical use according to claim 1, further comprising a removable insertion rod (36) extending outwards along the prolongation of an end piece of the inflation opening (22) and a removal placement wire (38) extending along the sole (30) or inside the sole.

* * * * *